(12) United States Patent
Daley

(10) Patent No.: US 7,143,640 B2
(45) Date of Patent: Dec. 5, 2006

(54) FLUID SAMPLING DEVICE, TUBULAR SAMPLING COUPON, AND SYSTEM AND METHOD FOR SAMPLING EQUIPMENT AND FLUID CONDITIONS

(75) Inventor: Ethan Daley, Cupertino, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 50 days.

(21) Appl. No.: 11/114,270

(22) Filed: Apr. 26, 2005

(65) Prior Publication Data

US 2006/0236787 A1  Oct. 26, 2006

(51) Int. Cl.
*G01N 17/00* (2006.01)
(52) U.S. Cl. .......................................... 73/86
(58) Field of Classification Search ............... 73/86
See application file for complete search history.

(56) References Cited

U.S. PATENT DOCUMENTS

| | | | | | |
|---|---|---|---|---|---|
| 2,484,279 | A | * | 10/1949 | Folz ............................... | 73/86 |
| 3,639,876 | A | * | 2/1972 | Wilson ........................... | 338/13 |
| 4,631,961 | A | * | 12/1986 | Yohe et al. ................. | 73/866.5 |
| 5,049,492 | A | * | 9/1991 | Sauer et al. .................... | 435/30 |
| 5,349,874 | A | * | 9/1994 | Schapira et al. ............... | 73/864 |
| 5,639,959 | A | * | 6/1997 | Reiber ............................ | 73/86 |
| 6,487,895 | B1 | * | 12/2002 | Brooker et al. ................ | 73/86 |

OTHER PUBLICATIONS

"Bacterial Monitoring General Information," Caproco Limited, Apr. 14, 2004; http://www.caproco.com/catalog/pdf/Bacterial-Monitoring/General-Information.pdf, 2 pages.
"High Pressure Biofilm Device BD-10SS," Tyler Research Corporation, Apr. 14, 2004; http://www.tylerresearch.com/docs/BD-10SS%20instructions.doc, 1 page.
"Industrial Biofouling," Jana Jass, Susanne Surman, and James Walker, eds. West Essex, UK; John Wiley & Sons, Ltd. 2000, pp. 1-12; 39-54; 79-83; 103-129.

* cited by examiner

*Primary Examiner*—Robert Raevis

(57) ABSTRACT

In one embodiment, a sampling device has first and second detachable body parts defining a fluid flow path. The first body part defines a fluid inlet of the fluid flow path and the second body part defines a fluid outlet of the fluid flow path. A diameter of a portion of the fluid flow path is enlarged to receive and retain a tubular sampling coupon that further defines the fluid flow path. The tubular sampling coupon may be of a type having first and second coupon body parts mated along a long axis. The tubular sampling coupon is of a size and shape to be received and retained within a fluid flow path of a sampling device, wherein the tubular sampling coupon further defines the fluid flow path. Systems and methods using the sampling device and sampling coupon are also disclosed.

16 Claims, 7 Drawing Sheets

FLUID SAMPLING DEVICE, TUBULAR SAMPLING COUPON, AND SYSTEM AND METHOD FOR SAMPLING EQUIPMENT AND FLUID CONDITIONS

BACKGROUND

Many types of equipment commonly found in a variety of industries emit heat during operation and may employ cooling techniques based on either air or liquid cooling mediums to maintain a stable operating temperature. Liquid cooling systems generally offer greater operating temperature stability over air cooling systems because of the higher heat transfer efficiency of liquid. The advantages of liquid cooling systems include greater system reliability, reduced operating costs, and longer equipment life span.

However, liquid cooling systems have disadvantages, including the formation of biofilms within the liquid cooling medium. Biofilms are collections of microorganisms and the extracellular polymers they secrete, which attach to a substrate. Biofilm-related problems cost billions of dollars annually by corroding pipes, reducing heat transfer or hydraulic pressure in industry cooling systems, plugging water injection jets, and clogging water filters. In addition, biofilms can cause major medical problems through infection harboring bacteria.

SUMMARY OF THE INVENTION

In one embodiment, a fluid sampling device comprises first and second detachable body parts defining a fluid flow path. The first body part defines a fluid inlet of the fluid flow path and the second body part defines a fluid outlet of the fluid flow path. A diameter of a portion of the fluid flow path is enlarged to receive and retain a tubular sampling coupon that further defines the fluid flow path.

In one embodiment, a tubular sampling coupon is disclosed. The tubular sampling coupon comprises first and second coupon body parts mated along a long axis. The tubular coupon is of a size and shape to be received and retained within a fluid flow path of a sampling device, wherein the tubular sampling coupon further defines the fluid flow path.

In another embodiment, a system for sampling fluid conditions comprises equipment having a fluid flow path, a sampling device, and a tubular sampling coupon. The sampling device comprises first and second detachable body parts defining a fluid flow path. The first body part defines a fluid inlet of the fluid flow path and the second body part defines a fluid outlet of the fluid flow path. A diameter of a portion of the fluid flow path is enlarged to receive and retain a tubular sampling coupon. The tubular sampling coupon further defines the fluid flow path and has first and second coupon body parts mated along a long axis. The fluid flow path of the equipment and the fluid flow path of the sampling device are coupled to one another.

In another embodiment a method for sampling a condition of equipment is disclosed. The method comprises: i) connecting a sampling device to equipment having a fluid flow path, wherein the sampling device comprises a chamber defining a fluid flow path and having a tubular sampling coupon positioned within the chamber and further defining the fluid flow path; and ii) after operating the equipment for a period of time wherein fluid is caused to circulate through the tubular sampling coupon, removing the tubular sampling coupon from the chamber defining the fluid flow path through the sampling device.

Other embodiments are also disclosed.

BRIEF DESCRIPTION OF THE DRAWINGS

Illustrative and presently preferred embodiments of the invention are illustrated in the drawings, in which.

DETAILED DESCRIPTION OF AN EMBODIMENT

It would be desirable to have a biofilm sampling device for sampling the growth of biofilms within liquid cooled systems, such as within semiconductor test systems, for example, to assist in properly targeting and eliminating the growth of biofilms.

Figure 1:
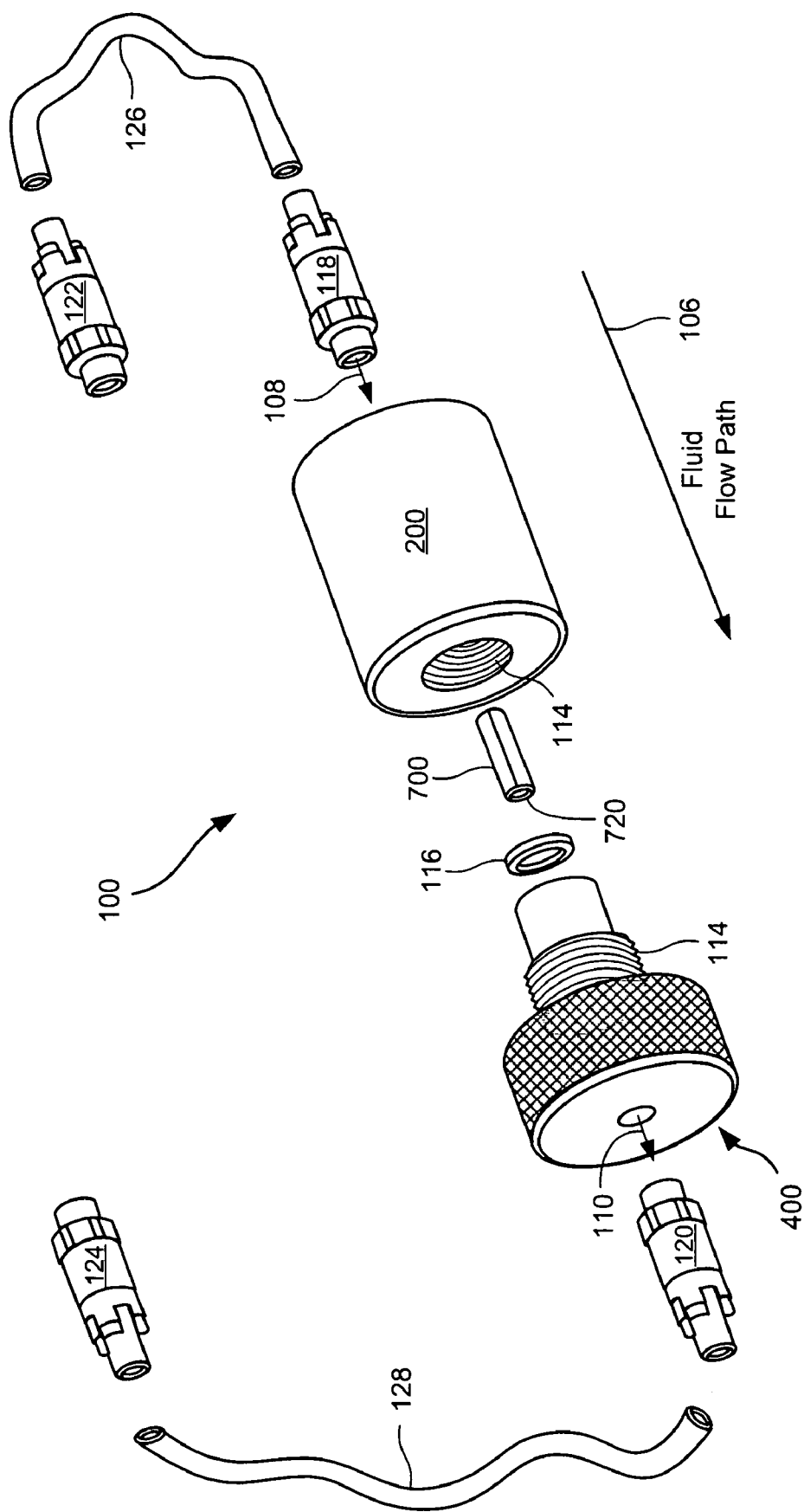
FIG. 1 illustrates an exploded perspective view of an exemplary embodiment of a sampler device.

The biofilm sampling device shown in FIG. 1 is designed to accurately sample biofilm growth within liquid-cooled equipment while minimally disrupting equipment operation. The sampling device provides a user with an accurate understanding of the type and extent of biofilms that may grow within liquid cooling systems used to cool equipment.

The sampling device generally contains a tubular sampling coupon and the sampling device and tubular sampling coupon together define a continuous fluid flow path, as shown in FIG. 1. The tubular sampling coupon will accumulate biofilm growth over a period of time and a user may then remove and analyze that tubular sampling coupon to extrapolate the type and extent of biofilms within a given piece of equipment. This sampling device is particularly advantageous because the sampling can be performed in situ, preventing costly shut-down and disassembly of the equipment.

FIG. 1 illustrates an exploded perspective view of an exemplary embodiment of a fluid sampling device 100. The sampling device 100 may comprise first and second detachable body parts 200, 400 defining a fluid flow path (represented by arrow 106) through sampling device 100. The first second detachable body parts 200, 400 of the sampling device 100 may comprise a rigid material, such as stainless steel, for example.

Figure 2:
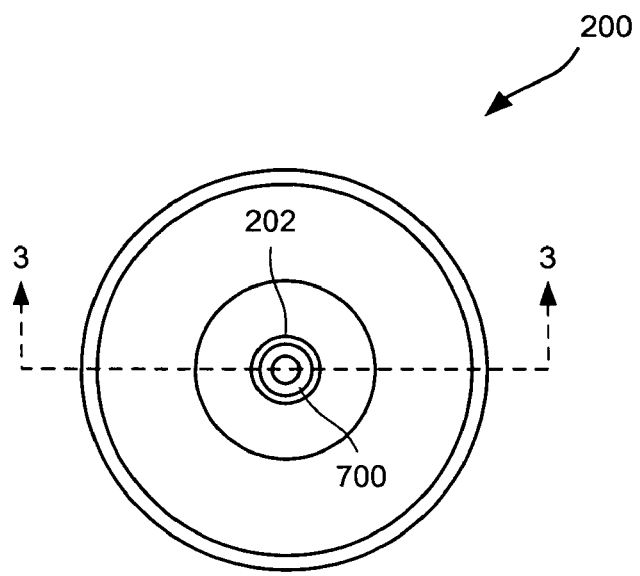
FIG. 2 illustrates an elevation view of a first detachable sampler body part of the sampler device of FIG. 1.
Figure 3:
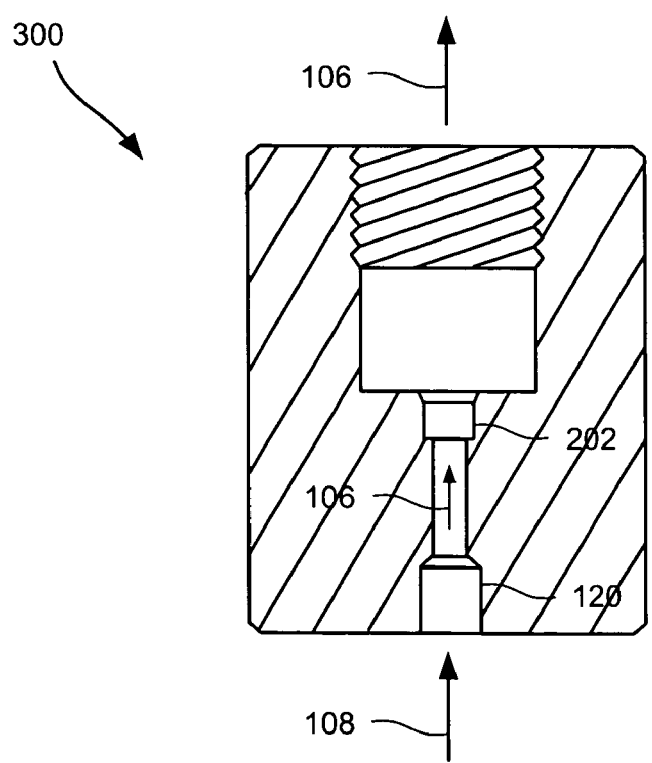
FIG. 3 illustrates a cross-sectional view of the first detachable sampler body part of FIG. 2.

The first body part 200 defines a fluid inlet (represented by arrow 108) of the fluid flow path 106 and is shown individually in FIGS. 2 & 3. The second body part 400 defines a fluid outlet (represented by arrow 110) of the fluid flow path 106 and is show individually in FIGS. 4 & 5. Both the first and second body parts 200, 400 have a diameter 202 (or chamber) of a portion of the fluid flow path 106 which is enlarged to receive and retain a tubular sampling coupon 700 that further defines the fluid flow path 106, as best shown in FIG. 6.

Figure 6:
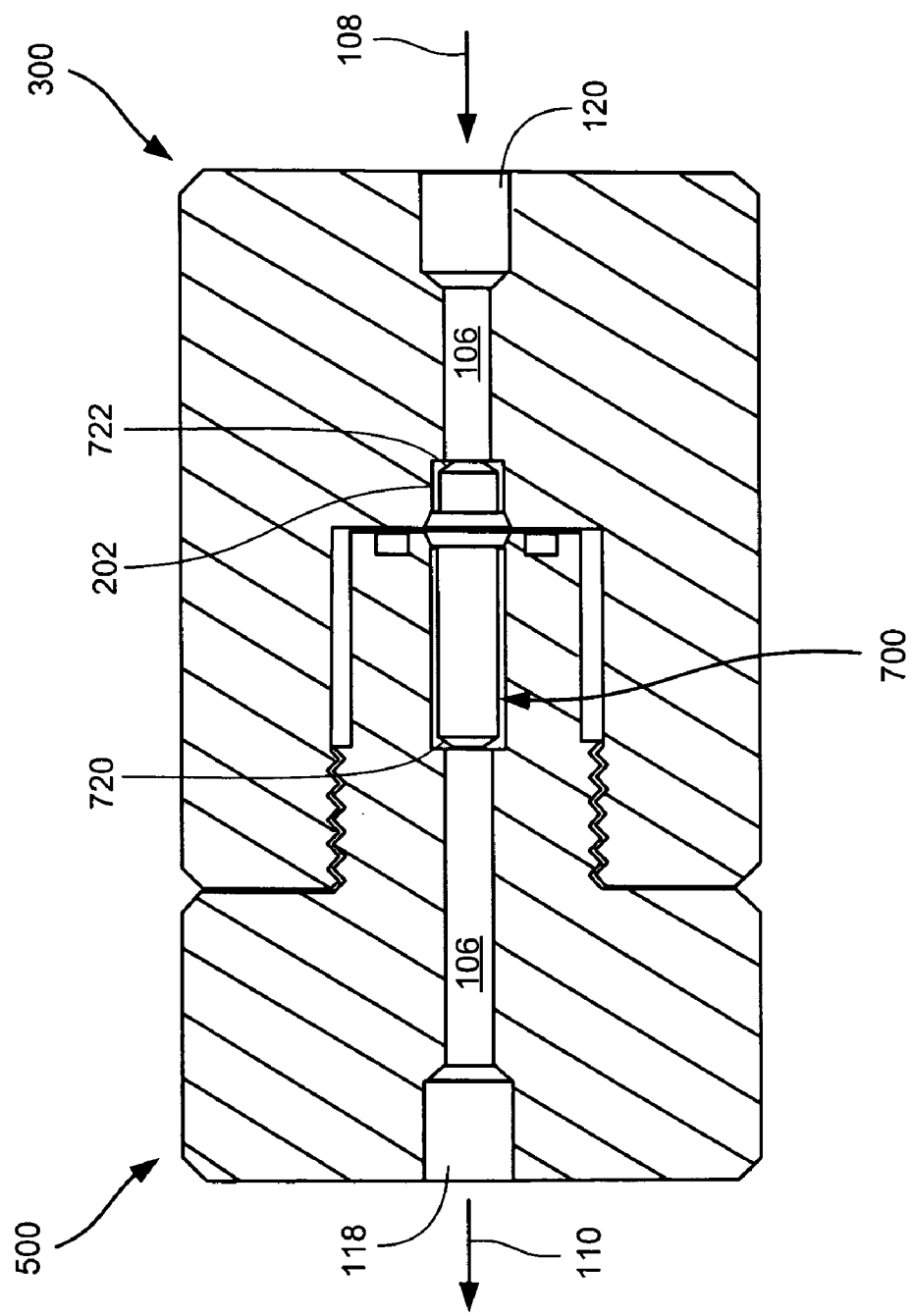
FIG. 6 illustrates a cross-sectional view of the coupling of the first and second detachable sampler body parts of the sampler device of FIG. 1.

The first and second detachable body parts 200, 400 are sized to be securely and detachably coupled together (shown in cross-section in FIG. 6). When the body parts 200, 400 are coupled together, the tubular sampling coupon 700 is securely retained with the chamber 202 concentric to the sampling device 100.

The first and second detachable body parts 200, 400 may be threaded (shown as threads 114), as shown in FIG. 1, and may be detachably coupled by screwing first and second body parts 200, 400 together by hand. To aid assembly and disassembly by hand, one of the body parts, such as second body part 400, may be knurled (shown in FIG. 4 as the cross-hatched portion). In an alternative embodiment, the first and second detachable body parts 200, 400 may be coupled together by an alternative mechanism, such as a clamp or clip (not shown) for example.

First and second detachable body parts 200, 400 may be easily separated to access the tubular sampling coupon 700. Separating the first and second detachable body parts 200, 400 may be done, for example, by unscrewing the first and second detachable body parts 200, 400. Separating the first and second detachable body parts 200, 400 is advantageous for examined and/or cleaned the interior of the sampling device 100.

Figure 7:
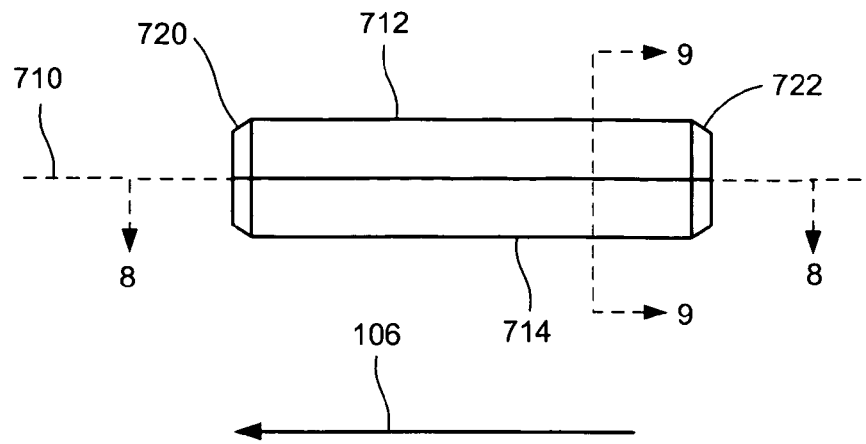
FIG. 7 illustrates a perspective view of a tubular sampling coupon.
Figure 8:
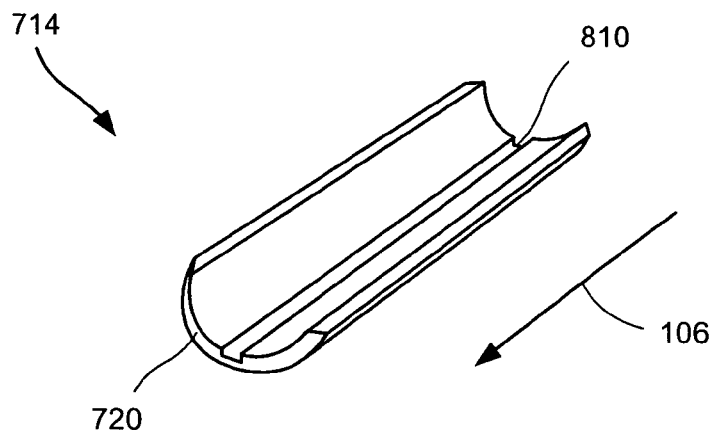
FIG. 8 illustrates a cross-sectional view of the tubular sampling coupon of FIG. 7.
Figure 9:
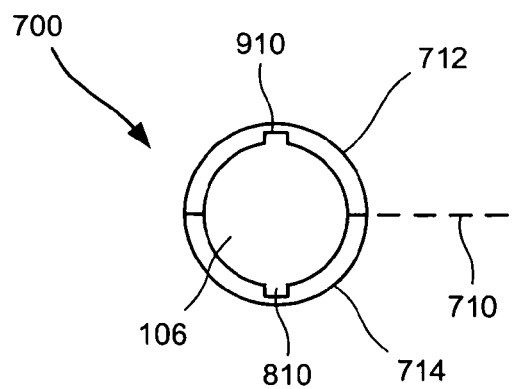
FIG. 9 illustrates an elevation view of the tubular sampling coupon of FIG. 7.

Sampling device 100 may further comprise tubular sampling coupon 700, as shown in FIGS. 1 & 7–9. With reference now to FIGS. 7–9, tubular sampling coupon 700 generally comprises a hollow tube divided along its long axis 710 to form first and second mated body parts 712, 714.

The design of the elongated hollow tubular sampling coupon 700 is advantageous because it provides a greater surface area for analysis than many available stud-style coupons, and because it provides a smooth, unobstructed fluid flow path 106 through the tubular sampling coupon 700 and the sampling device 100. The fluid flow path 106 through the sampling device 100 and the tubular sampling coupon 700 is of substantially uniform diameter.

The sampling device 100 and tubular sampling coupon 700 are designed to foster a fully developed fluid flow path 106 throughout, such that, despite traveling though multiple parts (first and second detachable sampler body parts 200, 400, and tubular sampling coupon 700), the fluid flow path 106 will act as a smooth continuous tube.

The tubular sampling coupon 700 is sized such that when tubular sampling coupon 700 is inserted into the chamber 202 within the sampling device 100, and the first and second detachable sampler body parts 200, 400 are coupled together, the chamber 202 is sized to press seal the two body parts of the tubular sampling coupon 712, 714 together to create a sealed tube. This is best shown in cross-section in FIGS. 6, 7, & 9. The first and second mated body parts 712, 714 are tightly and securely mated together within chamber 202 without the use of adhesives or other parts.

When the tubular sampling coupon 700 is removed from the sampling device 100, the first and second mated body parts 712, 714 easily come apart by hand, exposing the tubular sampling coupon's 700 wetted interior surface for analysis, as shown in FIG. 8. Alternatively, tubular sampling coupon 700 could be designed to be divided into more than two body parts. Separating first and second mated coupon body part 712, 714 is advantageous for cleaning as well as examination purposes. While the tubular sampling coupon 700 may be sterilized (such as in an autoclave) for reuse, this may not be desirable for a variety of reasons.

As shown in FIG. 8, at least one of the first and second mated coupon body parts 712, 714 may comprise a groove 810, wherein the groove 810 is formed in an inner wall of tubular sampling coupon 700, parallel to the fluid flow path 106. In one embodiment, both of the first and second mated coupon body parts 712, 714 may comprise grooves 810, 910 formed in an inner wall.

Placement of grooves 810, 910 within the tubular sampling coupon 700 such that they are parallel to the fluid flow path 106 ensures the smooth unobstructed flow of the fluid flow path 106. Grooves 810, 910 may take a variety of size and shapes and may, as shown in FIGS. 8 & 9 for example, comprise a flat bottom. Grooves 810, 910 further aid in the analysis of the tubular sampling coupon 700 because grooves 810, 910 provides an ideal micro-niche for biofilms to attach and grow within the coupon tubular sampling 700.

Tubular sampling coupon 700 may be formed from a softer metal (as compared to the first and second detachable sampler body parts 200, 400), such as aluminum, and may comprise beveled ends 720, 722, as shown in FIG. 7. When tubular sampling coupon 700 is inserted into the chamber 202 within the sampling device 100 and the first and second detachable sampler body parts 200, 400 are coupled together, the chamber 202 is sized to crush the ends of tubular sampling coupon 700 within the chamber 202 to form a crush seal. The beveled ends 720, 722 of tubular sampling coupon 700 mate against inner walls within the chamber 202 of the sampling device 100 and form a crush seal, as best shown in FIG. 6.

The crush seal provides one method of leak prevention for the sampling device 100. The crush seal helps prevent fluid from seeping into the gap between the first and second detachable body parts 200, 400. The presence of water in that gap could not only expose the fluid flow path 106 to the threads 114 used to couple the first and second detachable body parts 200, 400, but could also create a stagnant zone in the fluid flow path 106 (i.e. providing inaccurate biofilm sampling results).

Figure 4:
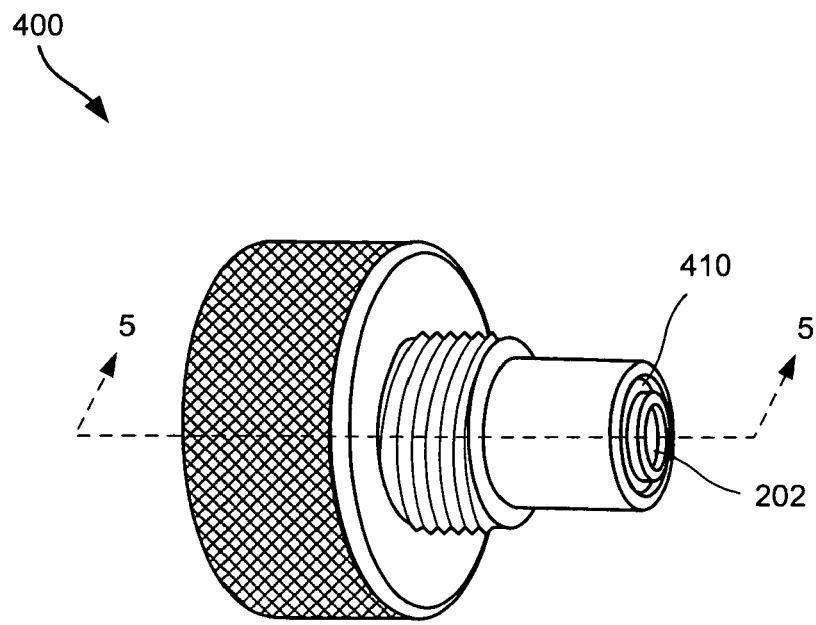
FIG. 4 illustrates an elevation view of a second detachable sampler body part of the sampler device of FIG. 1
Figure 5:
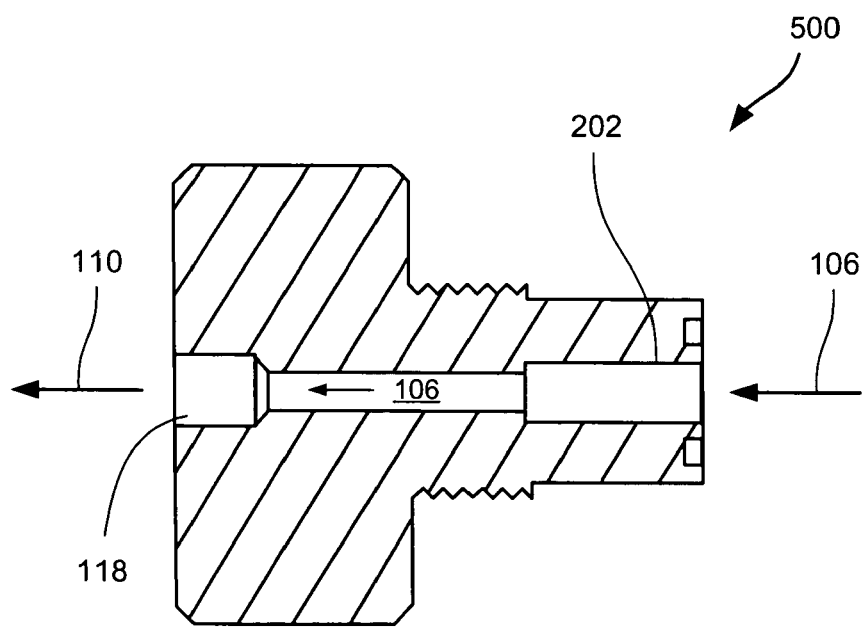
FIG. 5 illustrates a cross-sectional view of the second detachable sampler body part of FIG. 4.

The sampling device 100 may further comprise additional components, such as o-ring seal 116, shown in FIG. 1. O-ring seal 116 may comprise an elastomeric material suitable for sealing, such as rubber, for example. The o-ring seal 116 provides a second method of leak prevention for sampling device 100 by providing a water-tight seal in the gap between the first and second detachable body parts 200, 400 of sampling device 100. As best shown in FIG. 4, the o-ring seal 116 may be seated with a channel or gland 410 of the second body part 400.

Sampling device 100 may further comprise self-sealing quick connect mechanisms 118, 120 coupled to the ends of the sampling device 100, as shown in FIG. 1. As shown in FIGS. 1 & 6, self-sealing quick connect mechanism 118 may be detachably coupled to the fluid inlet end 108 of the sampling device 100, and self sealing quick connect mechanism 118 may be detachably coupled to the fluid outlet end 110 of the sampling device 100.

The self-sealing quick connect mechanisms 118, 120 may be detachably or releaseably coupled to each end of the sampling device 100. Providing these self-sealing quick connect mechanisms 118, 120 on the ends of the sampling device 100 provides the ability to connect and disconnect a variety of equipment (having a variety of different designs and different connection mechanisms) with the sampling device 100.

Figure 11:
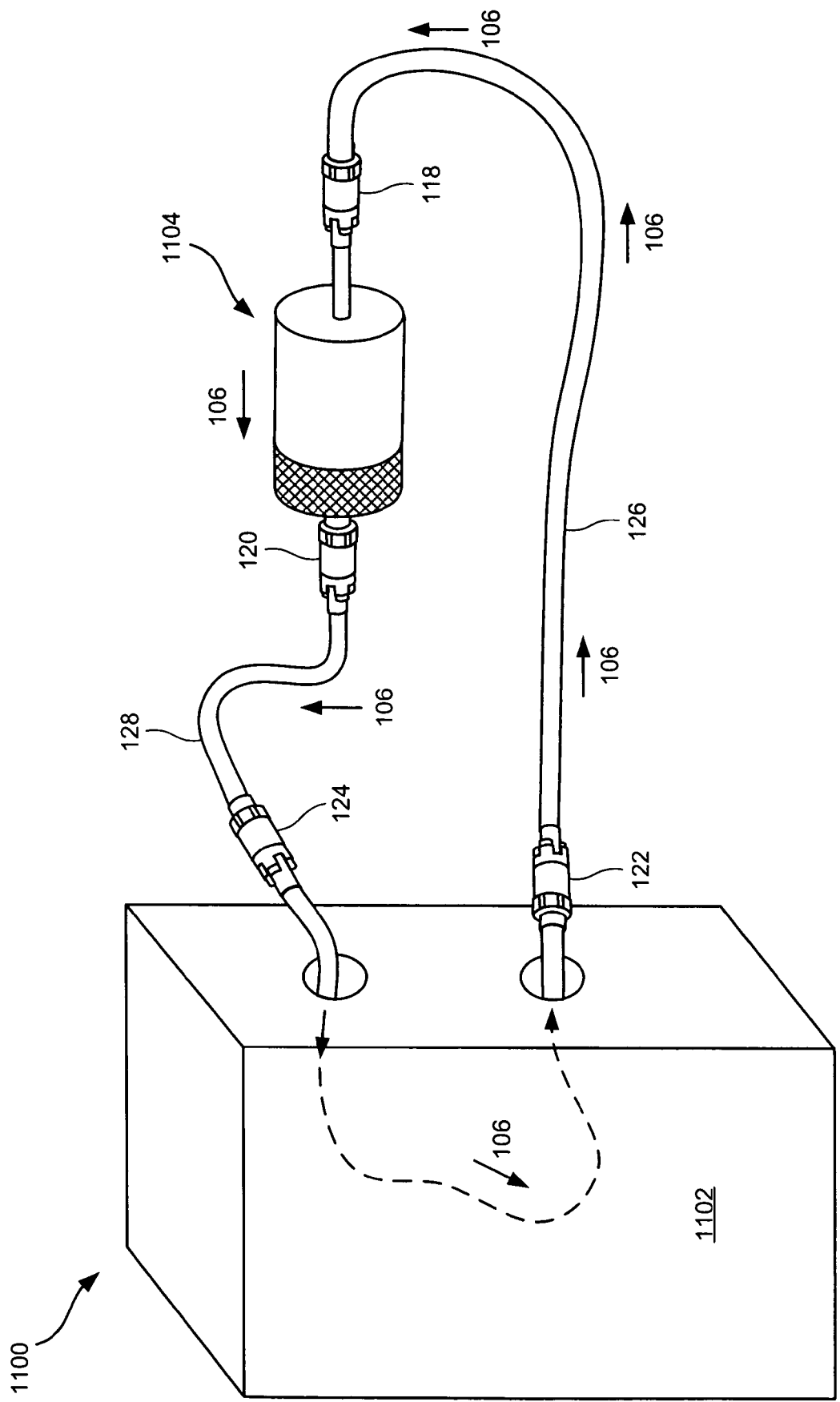
FIG. 11 illustrates a system for sampling equipment and fluid conditions.

The self-sealing quick connect mechanisms 118, 120 connected to sampling device 100 may additionally be coupled to a number of lengths of hose or tubing 126, 128 (as shown in FIG. 1) for flexibly connecting the sampling device 100 to equipment (as shown in FIG. 11). The hose 126, 128 may be a flexible hose or tubing structure having any diameter or length. The diameter and length of hose 126, 128 may be selected by a user based upon the specific equipment to be tested by the sampler device 100.

Additional self-sealing quick connect mechanisms 122, 124 may be coupled to opposite ends of the number of lengths of hose 126, 128 to provide the self-sealing quick connection to the equipment itself (often to a water manifold or 'water block' of equipment), as shown in FIG. 11.

The use of self-sealing quick connect mechanisms 118–124 allows the sampling device 100 to be connected in line with operating equipment quickly, even while the fluid is flowing. Thus, self-sealing quick connect mechanisms 118–124 minimize: i) disruption of operating equipment; and ii) the time delay between when a fluid flow is stopped and when a tubular sampling coupon is analyzed.

Biofilms tend to grow in the presence of moving fluids, thus stopping the fluid flow for long periods of time to connect and disconnect sampling equipment may cause the biofilms to detach and provide inaccurate sampling results. The self-sealing quick connect mechanisms 118–124 provide the sampling device 100 with the capability of being quickly connected and disconnected from operating equipment. The self-sealing quick connect mechanisms 118–124 provide the sampling device 100 with an additional advantage because they allow a user to sample, i) more efficiently and, ii) to obtain more accurate results by sampling the most representative possible picture of conditions within the equipment.

By minimizing the time delay between when a fluid flow is stopped and when the tubular sampling coupon 700 is exposed to testing (i.e. analysis, examination, extrapolation, microscopic review, etc.), the sampling device 100 can more accurately 'catch' the biofilm before it can slough off and go undetected.

Additionally, biofilms may form (or grow) differently on different materials. To maximize the accuracy of the results obtained by the sampling device 100, it is desirable to have a sampling device 100, tubular sampling coupon 700, and hoses 126, 128, formed from the same materials used within the fluid flow path 106 of the equipment.

Specifically, the first and second detachable body parts 200, 400 of the sampling device 100, the tubular sampling coupon 700, the self-sealing quick connect mechanisms 118–124, and the number of lengths of hose 126, 128, may all be selected to match the materials and flow diameters within the fluid flow path 106 of the equipment being tested. The use of the same materials in both the equipment and the sampling device 100 provides a user with a more thorough understanding of how specific biofilms grow on specific materials.

As shown in FIG. 11, a system 1100 for sampling fluid conditions may generally comprise a piece of equipment 1102 having a fluid flow path 106, the sampling device 100, 1104, and the tubular sampling coupon 700. The sampling device 100, 1104 as described above, has first and second detachable body parts 200, 400 defining fluid flow path 106 and having a diameter (i.e. chamber 202) of a portion of the fluid flow path 106 enlarged to receive and retain a tubular sampling coupon 700. The tubular sampling coupon 700 further defines the fluid flow path 106 and has first and second coupon body parts 712, 714 mated along a long axis 710, as described above.

With continuing reference to FIG. 11, the fluid flow path 106 of the equipment and the fluid flow path 106 of the sampling device 100 are coupled to one another (via self-sealing quick connect mechanisms 118–124 and hoses 126, 128) such that the fluid flow path 106 comprises a smooth unobstructed fluid flow path 106 of substantially uniform diameter.

Figure 10:
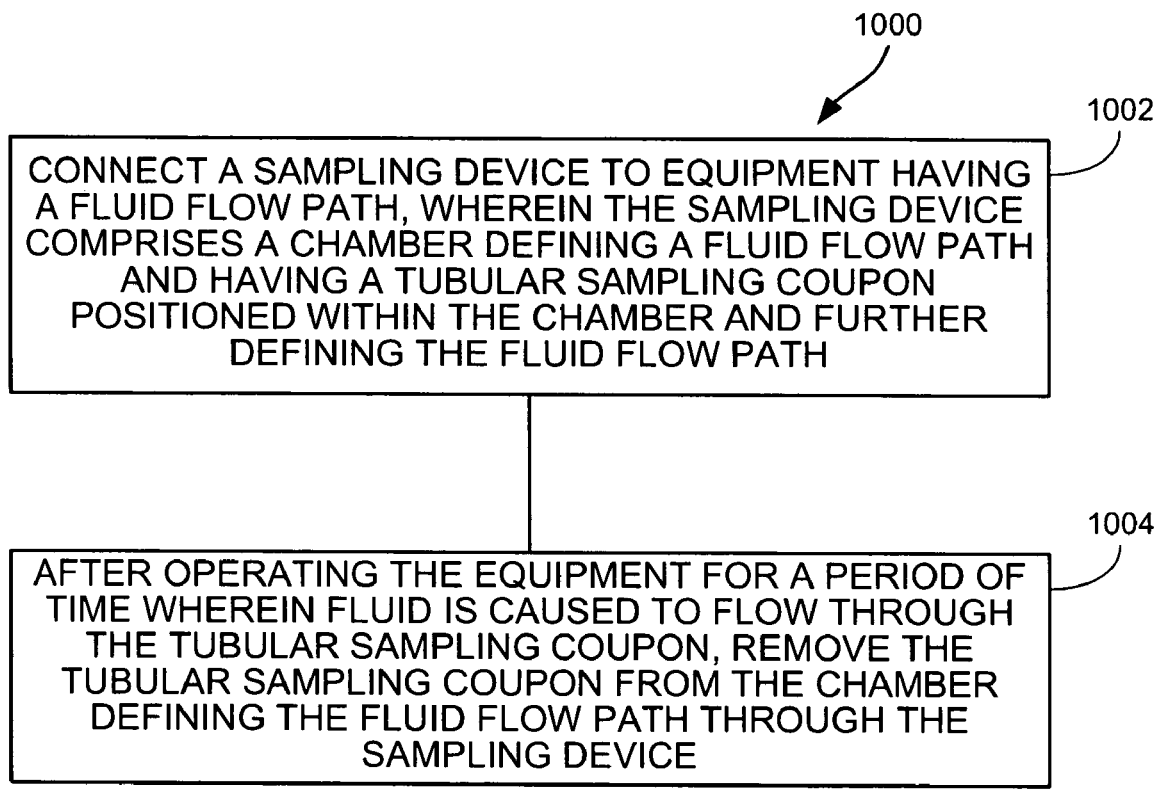
FIG. 10 illustrates a method for sampling a condition of equipment.

In one embodiment, a method 1000 for sampling a condition of equipment is also disclosed, as illustrated in FIG. 10. The method comprises connecting 1002 the sampling device 100 to equipment having a fluid flow path 106. A user may simply connect 1002 a sampling device 100 to equipment by connecting self-sealing quick connect mechanisms 122 & 124 to the equipment. Alternatively, a user may insert, remove, or exchange a tubular sampling coupon 700 from within the chamber 202 of the sampling device 100 before connecting the sampling device 100 to the equipment (via self-sealing quick connect mechanisms 122 & 124).

In operation, a user may access tubular sampling coupon 700 by detaching (e.g., by uncoupling or unscrewing) the first and second detachable body parts 200, 400 by hand. An operator may then insert, remove, or exchange a tubular sampling coupon 700 from within the chamber 202 of the sampling device 100. An operator may then re-couple sampling device 100 by coupling (e.g., screwing) the first and second detachable body parts 200, 400 back together.

Sampling device 100 provides an operator with the ability to connect or disconnect the sampling device 100 from equipment by either: i) detaching self-sealing quick connect mechanisms 118 & 120 closest to the sampling device 100, or ii) detaching the self-sealing quick connect mechanisms 122 & 124 closest to the equipment.

After operating the equipment for a period of time wherein fluid is caused to flow though tubular sampling coupon 700, the tubular sampling coupon 700 may then be removed 1004 from the chamber 202 defining the fluid flow path 106 through the sampling device 100, as referenced in FIG. 10. After removing the tubular sampling coupon 700, the tubular sampling coupon 700 may then be examined for the presence of biofilms and/or indications of corrosion. In alternative embodiments, the sampling device 100 may be used to analyze a plurality of different equipment conditions and may possibly be used as a filter.

Sampling device 100 is advantageous because it may be operated without the use of tools. No tools or other special equipment are required to: i) install or remove the tubular sampling coupon 700 from the sampling device 100, or ii) connect or disconnect the sampling device 100 with equipment.

Sampling device 100 is also advantageous because it: i) maintains fluid flow path conditions consistent with the fluid flow path conditions within the equipment to be tested; ii) provides the user with the ability to quickly connect and disconnect the sampling device 100 in line with operating equipment; iii) provides the user with the ability to quickly insert, remove, and exchange coupons, which minimizes equipment and fluid flow disruption; iii) provides accurate biofilm sampling results and/or corrosion results because biofilms (which vary considerably with flow properties such as velocity, pressure, viscosity, etc) tend to flourish in moving fluids and the tubular sampling coupon facilitates sampling of a moving fluid flow path.

What is claimed is:

1. A fluid sampling device, comprising:
    first and second detachable body parts defining a fluid flow path; wherein the first body part defines a fluid inlet of the fluid flow path, and the second body part defines a fluid outlet of the fluid flow path; and wherein a diameter of a portion of the fluid flow path is enlarged to receive and retain a tubular sampling coupon; and
    the tubular sampling coupon, wherein the tubular sampling coupon further defines the fluid flow path and is divided along an axis parallel to the fluid flow path to form first and second mated and separable body parts.

2. The sampling device of claim 1, wherein at least one of the first and second mated body parts of the tubular sampling coupon comprises a groove, wherein the groove is formed in an inner wall of the tubular sampling coupon, parallel to the fluid flow path.

3. The sampling device of claim 2, wherein the groove comprises a flat bottom.

4. The sampling device of claim 1, wherein the tubular sampling coupon comprises beveled ends, wherein the beveled ends of the tubular sampling coupon mate against inner walls of the sampler device and provide a crush seal between the tubular sampling coupon and the first and second detachable body parts.

5. The sampling device of claim 1, wherein the first and second detachable body parts comprise threaded portions, and wherein the threaded portions provide the detachable coupling of the first and second detachable body parts.

6. The sampling device of claim 1, further comprising an o-ring seal positioned between the first and second detachable body parts.

7. The sampling device of claim 1, further comprising at least one self-sealing quick connect mechanism for connecting and disconnecting the fluid flow path of the sampler device with a fluid flow path of equipment.

8. A tubular sampling coupon, comprising:
    first and second coupon body parts that are mated and separable along a long axis, wherein the tubular sampling coupon is of a size and shape to be received and retained within a fluid flow path of a sampling device, wherein the tubular sampling coupon further defines the fluid flow path, and wherein the long axis of the tubular sampling coupon is parallel to the fluid flow path.

9. The tubular sampling coupon of claim 8, wherein the tubular sampling coupon comprises beveled ends, wherein the beveled ends of the tubular sampling coupon are crushable to provide one half of a crush seal.

10. The tubular sampling coupon of claim 8, wherein at least one of the first and second coupon body parts comprises a groove, wherein the groove is formed in an inner wall of the tubular sampling coupon, parallel to the fluid flow path.

11. The tubular sampling coupon of claim 10, wherein the groove comprises a flat bottom.

12. A system for sampling fluid conditions, comprising:
    equipment having a fluid flow path;
    a sampling device having first and second detachable body parts defining a fluid flow path; wherein the first body part defines a fluid inlet of the fluid flow path, and the second body part defines a fluid outlet of the fluid flow path; and wherein a diameter of a portion of the fluid flow path is enlarged to receive and retain a tubular sampling coupon;
    a tubular sampling coupon that further defines the fluid flow path and has first and second coupon body parts that are mated and separable along an axis parallel to the fluid flow path; and
    wherein the fluid flow path of the equipment and the fluid flow path of the sampling device are coupled to one another.

13. The system of claim 12, wherein the fluid flow path of the sampling device is of substantially uniform diameter.

14. The system of claim 12, wherein the tubular sampling coupon is formed of a material that is matched to a material in the fluid flow path of the equipment.

15. The system of claim 12, further comprising a number of self-sealing quick connect mechanisms for operably connecting and disconnecting the sampling device to the equipment.

16. The system of claim 12, further comprising a number of lengths of hose flexibly connecting the sampling device with the equipment, wherein the number of lengths of hose are formed of a material that is matched to a material in the fluid flow path of the equipment.

* * * * *